(12) United States Patent
Tai et al.

(10) Patent No.: US 7,709,538 B2
(45) Date of Patent: May 4, 2010

(54) ST104P, AN ANTI-ANGIOGENIC AGENT

(75) Inventors: Ming-Hong Tai, Kaohsiung (TW); Su-Ying Liu, Taipei Shien (TW)

(73) Assignee: Sagittarius Life Science Corp., Taipei Shien (TW)

( * ) Notice: Subject to any disclaimer, the term of this patent is extended or adjusted under 35 U.S.C. 154(b) by 56 days.

(21) Appl. No.: 12/172,948

(22) Filed: Jul. 14, 2008

(65) Prior Publication Data

US 2008/0269350 A1 Oct. 30, 2008

Related U.S. Application Data

(60) Continuation-in-part of application No. 11/830,334, filed on Jul. 30, 2007, now abandoned, and a division of application No. 10/865,480, filed on Jun. 8, 2004, now Pat. No. 7,273,890.

(51) Int. Cl.
*A61K 31/05* (2006.01)
(52) U.S. Cl. .................................................. 514/732
(58) Field of Classification Search ................... 514/732
See application file for complete search history.

(56) References Cited

U.S. PATENT DOCUMENTS

| | | | | | |
|---|---|---|---|---|---|
| 5,166,173 | A | * | 11/1992 | Hwang et al. | 514/510 |
| 5,196,452 | A | * | 3/1993 | Hwang et al. | 514/577 |
| 5,312,837 | A | * | 5/1994 | Hwang et al. | 514/577 |
| 5,409,959 | A | * | 4/1995 | Hwang et al. | 514/732 |
| 5,441,983 | A | * | 8/1995 | Hwang et al. | 514/562 |
| 6,469,045 | B1 | * | 10/2002 | D'Amato | 514/416 |

OTHER PUBLICATIONS

Pandya et al. Vascular Pharmacology, 2006, vol. 44, pp. 265-274.*
Gupta et al. Postgrad. Med. J., 2005, vol. 81, pp. 236-242.*

Thomas A. Ciulla et al., Anti-vascular endothelial growth factor therapy for neovascular ocular diseases other than age-related macular degeneration, Current Opinion in Ophthalmology, 2009, pp. 166-174, vol. 20.

Ashley J. Duits et al., Serum levels of angiogenic factors indicate a pro-angiogenic state in adults with sickle cell disease, British Journal of Haematology, 2006, 116-119, 134, Blackwell Publishing Ltd.

Richard F. Spaide et al., Prospective Study of Intravitreal Ranibizumab as a Treatment for Decreased Visual Acuity Secondary to Central Retinal Vein Occlusion, Am J Ophthalmol, 2009, 298-306, vol. 147, Elsevier Inc.

Jan S.A.G. Schouten et al., A systematic review on the effect of bevacizumab in exudative age-related macular degeneration, Graefes Arch Clin Exp Ophthalmol, 2009,1-11, vol. 247.

Pedro R. Moreno et al., Neovascularization in Human Atherosclerosis, Circulation, 2006, 2245-2252, vol. 113.

Gaelle Clavel et al., Angiogenesis markers (VEGF, soluble receptor of VEGF and angiopoietin-1) in very early arthritis and their association with inflammation and joint destruction, Clinical Immunology, 2007, 158-164, vol. 124.

M. Murata M.D., Ph.D. et al., The potential role of vascular endothelial growth factor (VEGF) in cartilage How the angiogenic factor could be involved in the pathogenesis of osteoarthritis?, Osteoarthritis and Cartilage, 2008, pp. 279-286, vol. 16.

Felix Bock Ph.D. et al., Corneal (Lymph)angiogenesis—From Bedside to Bench and Back: A Tribute to Judah Folkman, Lymphatic Research and Biology, 2008, 191-201, vol. 6, No. 3-4.

* cited by examiner

*Primary Examiner*—James D Anderson
(74) *Attorney, Agent, or Firm*—WPAT, P.C.; Anthony King

(57) ABSTRACT

The present invention relates to a method of treating a non-tumor condition or disease associated with angiogenesis in a human or animal comprises administering thereto an effective angiogenesis inhibiting dose of a tetrameric cyclic compound of 4,5-dihydroxynaphthalene-2,7, disulfonic acid linked by methylene bridges in a pharmaceutically acceptable carrier.

14 Claims, 11 Drawing Sheets

A

A

PBS

ST104P

EA.hy926

B

PBS

ST104P

BAEC

A

EA.hy926

B

BAEC

A

B.

A

B

ST104P, AN ANTI-ANGIOGENIC AGENT

CROSS-REFERENCE TO RELATED APPLICATIONS

This application is a Continuation-In-Part of the U.S. patent application Ser. No. 11/830,334 filed on Jul. 30, 2007, a Divisional of the U.S. patent application Ser. No. 10/865,480 filed on Jun. 8, 2004, now Patented as U.S. Pat. No. 7,273,890 on Sep. 25, 2007, and is hereby incorporated by reference in its entirety.

Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of the entire prior art of record and any search that the Office deems appropriate.

FIELD OF THE INVENTION

This invention relates to pharmacology and medicine. In particular, it relates to a method and a pharmaceutical compound exhibiting remarkable anti-angiogenic activity useful for cancer therapy as well as for diseases or conditions caused by excessive angiogenesis.

BACKGROUND OF INVENTION

Angiogenesis, the recruitment of new blood vessels, is an essential component of the metastatic pathway (Zetter, B. R., Annu Rev Med, 49, 407-424 (1998)). Persistent, unregulated angiogenesis occurs in a multiplicity of disease states, tumor metastasis and abnormal growth by endothelial cells and supports the pathological damage seem in these conditions. These vessels provide the principal route by which tumor cells exit the primary tumor site and enter the circulation. For many tumors, the vascular density can provide a prognostic indicator of metastatic potential, with the highly vascular primary tumors having a higher incidence of metastasis than poorly vascular tumors. Tumor angiogenesis is regulated by the production of angiogenic stimulators including members of the fibroblast growth factor and vascular endothelial growth factor families. In addition, tumors may activate angiogenic inhibitors such as angiostatin and endostatin that can modulate angiogenesis both at the primary site and at downstream sites of metastasis. The potential use of these and other natural and synthetic angiogenic inhibitors as anticancer drugs is currently under intense investigation. Such agents may have reduced toxicity and be less likely to generate drug resistance than conventional cytotoxic drugs.

In addition, angiogenesis has been associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

Excessive angiogenesis or abnormal growth of new blood vessels has also contributed to a variety of other diseases or conditions that are commonly known in the art to be associated with or otherwise mediated by angiogenesis. One such example is ocular neovascular disease. This disease is characterized by invasion of new blood vessels into the structures of the eye such as the retina or cornea. In age-related macular degeneration, the associated visual problems are caused by an ingrowth of choroidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasias. Other diseases or medical conditions associated with angiogenesis known in the art include, but without limitation to, rheumatoid arthritis, systemic lupus, polyarteritis, sickle cell anemia, osteoarthritis, vein occlusion, artery occlusion, carotid obstructive disease and atherosclerosis. Therapies directed at control of the angiogenic process could lead to the abrogation or mitigation of these diseases and conditions. Clinical trials are now underway to develop optimum treatment strategies for antiangiogenic agents (U.S. Pat. No. 6,518,298).

ST104P {(tetrameric cyclic compound of 4,5-dihydroxynaphthalene-2, 7, disulfonic acid linked by methylene bridges (Poh B.-L., et al, Tetra. Letters 30(8):1005-1008 (1989), Poh, B.-L., and Lim, C. S., Tetrahedron 46(10):3651-3658 (1990a), and Poh, B.-L., et al, *Tetrahedron* 46(12):4679-4386 (1990b)} is a synthetic polysulfated-, cyclo-, tetrachromotropylene macrocyclic compound containing four naphthalene units in its cyclic structure. It is a water soluble compound with marginal cellular toxicity. The functions of ST104P as anti-viral agents and anti-thrombotic treatment have been indicated in previous studies (U.S. Pat. Nos. 5,166,173, 5,196,452, 5,312,837, 5,441,983 and 5,409,959). However, ST104P has never been indicated to be an anti-angiogenic agent exhibiting anti-angiogenic functions useful for treatment of various diseases or conditions caused by or in association with undesirable angiogenesis including, but not limited to, cancer, age-related macular degeneration, diabetic retinopathy.

SUMMARY OF THE INVENTION

The present invention provides a method of treating a non-tumor condition or disease associated with angiogenesis in a human or animal comprises administering thereto an effective angiogenesis inhibiting dose of a tetrameric cyclic compound of 4,5-dihydroxynaphthalene-2,7, disulfonic acid linked by methylene bridges in a pharmaceutically acceptable carrier.

DETAILED DESCRIPTION OF THE INVENTION

Figure 1:
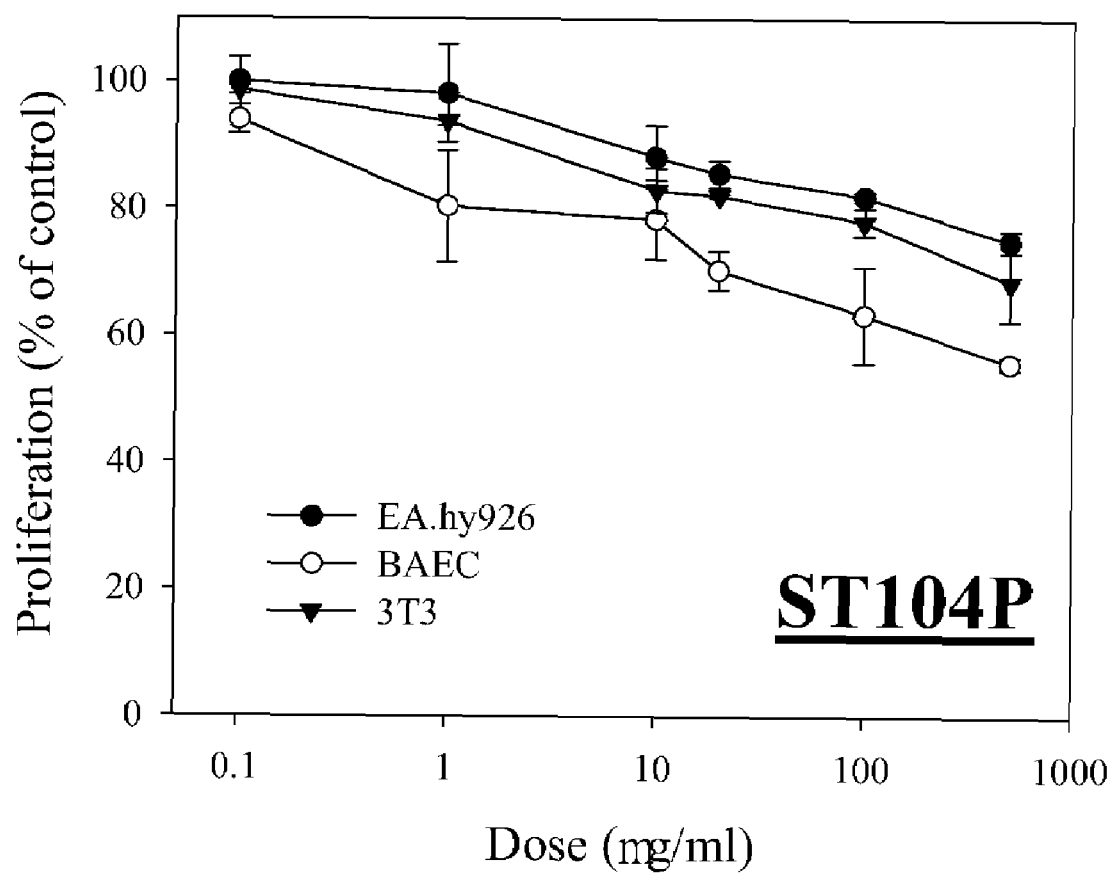
FIG. 1. The cytotoxicity of ST104P in different types of cells. (A) ST104P altered the morphologies of endothelial cells but not 3T3 cells. After treatment of ST104P at 10-500 μg/ml in DMEM medium containing 10% FCS for 24 h, the morphologies of BAEC and 3T3 cells were monitored under phase contrast microscopy. The pictures were taken at 400× magnification. (B) The dose-dependent effect of ST104P on the proliferation of different cells. After treatment with ST104P at 10-500 μg/ml or PBS for 48 h, the viability of various cells was determined by crystal violet method in an ELISA reader. Each data represent mean±SD of quadruplicate experiments. Asterisks indicated statistic significance versus control (P<0.001).

It is an object of the invention to provide for a composition comprising ST104P exhibiting a remarkable activity against diseases or conditions mediated by or in connection with angiogenesis including, without limitation, cancers, diabetic retinopathy, age-related macular degeneration, rheumatoid arthritis, osteoarthritis, atherosclerosis, corneal neovascularization, retinal/choroidal neovascularization and systemic lupus.

This invention relates to an anti-angiogenic function of a polysulfated, cyclic compound, ST104P that exhibits angiogenesis inhibition in vitro and in vivo without overt cytotoxicity. ST104P exhibits excellent water solubility and low cytotoxicity to endothelial cells while potently inhibited the secretion of matrix metalloproteinase (MMPs) by endothelial cells. Moreover, ST104 also perturbed the migration and tube formation of endothelial cells. Application of ST104P abolished the neovascularization in chicken choroiallantoic membrane (CAM) in a dose-dependent manner. Furthermore, repeated administration of ST104P into Lewis lung carcinoma resulted in delayed tumor growth and prolonged the life span of tumor-bearing mice. ST104P also significantly inhibited bFGF induced corneal neovascularization when applied either as implant or topical eye drops. These results indicated that ST104P inhibited angiogenesis and is useful for treatment of cancer and other diseases and conditions mediated by angiogenesis.

One aspect of the invention is to provide for an anti-tumor agent for treating tumors in a human or animal by the inhibition of angiogenesis in said tumors comprising a tetrameric cyclic compound of 4,5-dihydroxynaphthalene-2,7, disulfonic acid linked by methylene bridges in a pharmaceutical acceptable carrier. The pharmaceutical acceptable carrier may be adapted for oral, sublingual, rectal, nasal or parenteral (intravenous, intraperitoneal, intratumor) administration. Additionally, the pharmaceutical acceptable carrier may be adapted in the form of a tablet, a capsule, a cachet, a solution, an emulsion, a depository, or a powder.

Another aspect of the invention is to provide for a an angiogenesis inhibitor for inhibiting angiogenesis in tumors in a human or animal comprising a tetrameric cyclic compound of 4,5-dihydroxynaphthalene-2,7, disulfonic acid linked by methylene bridges in a pharmaceutical acceptable carrier. The pharmaceutical acceptable carrier may be adapted for oral, sublingual, rectal, vaginal, nasal or parenteral (intravenous, intraperitoneal, intratumor) administration. Additionally, the pharmaceutical acceptable carrier may be adapted in the form of a tablet, a capsule, a cachet, a solution, an emulsion, a depository, or a powder.

One more aspect of the invention is to provide for an angiogenesis inhibitor for treating a non-tumor condition or disease associated with angiogenesis in a human or animal comprising a tetrameric cyclic compound of 4,5-dihydroxynaphthalene-2,7, disulfonic acid linked by methylene bridges in a pharmaceutical acceptable carrier. The undesirable condition or disease associated with angiogenesis according to the present invention includes, but not limited to, polyarteritis, sickle cell anemia, vein occlusion, artery occlusion, carotid obstructive disease, atherosclerosis, corneal neovascularization, rheumatoid arthritis, systemic lupus, and osteoarthritis. The pharmaceutical acceptable carrier used hereto in connection with treatment of a non-tumor condition or disease associated with angiogenesis may be adapted for oral, sublingual, rectal, vaginal, nasal transdermal, ophthalmic (topical, intravitreal, intracameral) or parenteral administration. Additionally, the pharmaceutical acceptable carrier may be adapted in the form of a tablet, a capsule, a cachet, a solution, an emulsion, a depository, a patch, an implant, eye drop or a powder.

One further aspect of the invention is to provide for a method of treating tumors in a human or animal by the inhibition of angiogenesis in said tumors, which comprises administering thereto an effective angiogenesis inhibiting dose of a tetrameric cyclic compound of 4,5-dihydroxynaphthalene-2,7, disulfonic acid linked by methylene bridges in a pharmaceutical acceptable carrier. The pharmaceutical acceptable carrier used hereto in connection with treatment of tumors associated with angiogenesis may be adapted for oral, sublingual, rectal, vaginal, nasal or parenteral (intravenous, intraperitoneal, intratumor) administration. Additionally, the pharmaceutical acceptable carrier may be adapted in the form of a tablet, a capsule, a cachet, a solution, an emulsion, a depository, or a powder.

One further aspect of the invention is to provide for a method of inhibiting angiogenesis in tumors in a human or animal comprising administering thereto an effective angiogenesis inhibiting dose of a tetrameric cyclic compound of 4,5-dihydroxynaphthalene-2,7, disulfonic acid linked by methylene bridges in a pharmaceutical acceptable carrier that may be adapted for oral, sublingual, rectal, vaginal, nasal or parenteral (intravenous, intraperitoneal, intratumor) administration. Additionally, the pharmaceutical acceptable carrier may be adapted in the form of a tablet, a capsule, a cachet, a solution, an emulsion, a depository, or a powder.

One further aspect of the invention is to provide for a method of treating a non-tumor condition or disease associated with angiogenesis in a human or animal which comprises administering thereto an effective angiogenesis inhibiting dose of a tetrameric cyclic compound of 4,5-dihydroxynaphthalene-2,7, disulfonic acid linked by methylene bridges in a pharmaceutical acceptable carrier. According to the present invention, the undesirable condition or disease associated with angiogenesis that may be benefited from the method includes, but not limited to, diabetic retinopathy, age-related macular degeneration, polyarteritis, sickle cell anemia, vein occlusion, artery occlusion, carotid obstructive disease, atherosclerosis, corneal neovascularization, rheumatoid arthritis, systemic lupus, and osteoarthritis.

The pharmaceutical acceptable carrier used hereto in connection with treatment of a non-tumor condition or disease associated with angiogenesis may be adapted for oral, sublingual, ophthalmic (including topical, intravitreal or intracameral), rectal, vaginal, nasal, transdermal, or parenteral administration. The formulations may conveniently be presented in unit dosage form and may be prepared by conventional pharmaceutical techniques. Such techniques include the step of bringing into association the active ingredient and the pharmaceutical carries(s) or excipient(s). Additionally, the pharmaceutical formulations adapted by the invention suitable for oral or topical administration may be presented as discrete units in the form of a tablet, a capsule, a cachet, a solution, an emulsion, a depository, a patch, an implant, eye drop or a powder each containing a predetermined amount of the active ingredient, etc. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

EXAMPLES

Example 1

Materials and Methods

Reagents

Recombinant basic fibroblast growth factor (bFGF) was purchased from R&D System (Minneapolis, Minn.). Matrigel was from BD PharMingen (La Jolla, Calif.). The stock solution of ST104P is prepared in normal saline or phosphate buffered saline at 1 mg/ml or at such other concentrations or in such other different formulations as deemed desirable and appropriate according to the purposes of the intended assays.

Cell Culture

Human umbilical vein endothelial cells (HUVEC; passage 3 to 6) were isolated from umbilical veins and cultured in RPMI 1640 medium (Life Technologies, Gaithersburg, Md.) containing 15% fetal calf serum, 20 U/ml porcine heparin (Sigma Chemical Co), and 100 µg/ml endothelial cell growth supplement (Calbiochem; La Jolla, Calif.). Bovine aortic endothelial (BAEC) cells, 3T3 cells, and LL2 Lewis lung carcinoma cells were cultured with DMEM (Dulbecco's Modified Eagle Medium; Gibco BRL, Rockville, Md.) containing 10% fetal calf serum (PAA, Austria), 2 mM glutamine, 100 U/ml penicillin and 100 µg/ml streptomycin (Gibco BRL, Rockville, Md.) in 5% $CO_2$ at 37° C. Human vascular endothelial EA.hy926 cells were cultured in DMEM (Dulbecco's Modified Eagle Medium; Gibco BRL, Rockville, Md.) containing 10% fetal calf serum (PAA, Austria), 100 µM sodium hypoxanthine, 0.4 µM aminopterin, 16 µM thymidine (HAT; Gibco BRL, Rockville, Md.), 2 mM glutamine, 100 U/ml penicillin and 100 µg/ml streptomycin (Gibco BRL, Rockville, Md.) in 5% $CO_2$ at 37° C.

Cell Proliferation Assay

The effect of ST104P on the viability of various cells was determined using crystal violet stain assay. Briefly, cells cultured in 96-well plate (2-4×10$^3$ cells/well) were treated with various doses of ST104P for 48 h. After treatment, cells were fixed with 2.5% glutaraldehyde at room temperature for 15 minutes, stained with 0.1% crystal violet solution (in 20% methanol; 20 µl per well) for 20 minutes, washed with distilled water for three times, solublized with solution containing 50% ethanol and 0.1% acetic acid. The dye in viable cells was measured by reading the optical density at 590 nm using a scanning multi-well spectrophotometer (ELISA reader; Dynatech Laboratories, Chantilly, Va.).

Cell Migration Assay

Endothelial cells were treated with ST104P of indicated doses for 6-12 h, harvested by trysinization, collected by centrifugation, resuspended in DMEM media containing 0.1% BSA, and seeded in triplicate for each dose and controls in the upper compartment of the chamber ($1.2 \times 10^5$ cells in 400 µl). The lower compartment was filled with 200 µl of the DMEM media containing 100 ng/ml bFGF (R&D, Minneapolis, Minn.) as the chemoattractant, or with DMEM media containing 0.1% BSA as the negative control (to evaluate random migration). The compartments were separated by a polycarbonate filter (8-µm pore size; Nucleopore, Costar, Cambridge, Mass.) coated with 0.005% gelatin to allow cell adhesion. After incubation for 2-4 h in a humidified 5% $CO_2$ atmosphere at 37° C., cells on the upper side of the filter were removed, and those that had migrated to the lower side were fixed in absolute ethanol, stained with 10% Giemsa solution (Merck, Germany), and counted as a mean±SD per filter under five different high power fields.

Tube Formation Assay

Matrigel (Becton Dickinson; Bedford, Mass.) was diluted with cold serum-free medium to 10 mg/ml. Two hundred µl of the diluted solution were added to each well in 24-well plate and allowed to form a gel at 37° C. for 30 min. BAEC or HUVEC ($1.5 \times 10^5$ cells per ml) were initially incubated for 15 min with various doses of ST104P in complete medium. Two hundred µl of the cell suspension ($3 \times 10^4$ cells) were then subsequently added to each well and incubated for 6-8 h at 37° C. in 5% $CO_2$. Under these conditions endothelial cells form delicate networks of tubes that are detectable within 2-3 h and are fully developed after 8-12 h. After incubation with ST104P, the wells were washed and the Matrigel and its endothelial tubes were fixed with 3% paraformaldehyde.

Matrix Metalloproteinases (MMPs) Zymography

Secretion of MMPs by endothelial cells was assessed by 0.1% gelatin-SDS-PAGE zymography. Briefly, endothelial cells near 80% confluence were washed twice with serum-free media and treated with various doses of vasostatin for 24-48 h. Conditioned media were collected and assayed for protein concentration by Bradford assay. Aliquots of conditioned media were subjected to separation with 10% SDS-PAGE containing 0.1% type A gelatin (Sigma; St. Louis, Mo.). After electrophoresis, gel was washed twice with 2.5% Triton X-100, incubated in buffer containing 40 mM Tris-HCl, pH 8.0, mM $CaCl_2$, 0.01% sodium azide at 37° C. for 12-24 h, stained with 0.25% Coomassie Blue R-250 in 50% methanol and 10% acetic acid for 1 h, and destained with 10% acetic acid, 20% methanol. The gelatinolytic regions by MMPs were visualized as white bands in blue background.

Chorioallantoic Membrane (CAM) Assay

The CAM assay was carried out as described previously (Sheu et al., Anticancer Res 18, 4435-4441, 1998). Briefly, fertilized White Leghorn chicken eggs were purchased from Taiwan Provincial Research Institute for Animal Health (Hsin-Chu, Taiwan) and incubated at 37° C. with 60% humidity. On day 3, a square window was opened in the shell, and 2 to 3 ml of albumen was removed to allow detachment of the developing CAM. The window was sealed with a glass, and the eggs were returned to the incubator. On day 8, 50-100 µg ST104P in saline was injected onto the top of the CAM. The CAMs were examined daily until day 10-12, when the angiogenic response peaks, and photographed in ovo with a stereomicroscope equipped with Zeiss MC63 camera system (Zeiss, Oberkochen, Germany). The experiments were carried out using 10 eggs per group. In the presence of angiogenesis inhibitors, massive loss of vascular structure occurred and leaded to mortality of chicken embryos, which was used as another index to evaluate the extent of angiogenesis inhibition.

Animal Studies

Animal study was carried out in the animal facility of Kaohsiung Veterans General Hospital in accordance with institutional guidelines. Male C57BL/6J mice (6- to 8-week-old; Animal Center of National Cheng Kung University, Taiwan) were used. Mice were acclimated and caged in groups of four or less. All mice were fed with a diet of animal chow and water ad libitum. Animals were anesthetized in a methoxyflurane chamber prior to all procedures and were observed until fully recovered. Animals were sacrificed by a lethal dose of methoxyflurane.

Treatment of Lewis Lung Carcinoma

C57BL/6J mice were implanted with Lewis lung carcinomas cells using the techniques described previously (O'Reilly et al., Cell 88, 277-285, 1997). Briefly, the LL2 Lewis lung carcinoma cells were resuspended in PBS at the concentration of $2.5 \times 10^6$ cells per ml and injected into C57Bl6/J mice (n=20) with 0.1 ml of the cell suspension to induce tumor. Tumors were measured with a dial-caliper and volumes were determined using the formula width$^2 \times$length$\times$ 0.52. After tumor volumes reached 100-200 mm$^3$, mice were randomized into two groups receiving periodic injection of ST104P (n=10) or saline (n=10) by subcutaneous injection at a site near tumor. The measurement of tumor size was terminated when mice began to die. In addition, the survival rate of mice in different groups was recorded and analyzed by Kaplan-Mier Survival analysis.

Results

Low Cytotoxicity of ST104P in Different Types of Cells

We investigated the effects of ST104P in endothelial cells including BAEC, HUVEC, EA.hy926 cells, and in non-endothelial cells including 3T3 cells, GH3 cells, C6 cells, HepG2 cells, SK-Hep-1 cells, MDCK cells. Morphological analysis indicated that ST104P are not very toxic to all types of cells (data not shown). Application of ST104P moderately inhibited the proliferation in different types of cells in a dose-dependent manner (FIG. 1). However, ST104P treatment failed to elicit significant cytotoxicity that the $IC_{50}$ for ST104P in BAEC, EA.hy926, and 3T3 cells were much larger than 500 µg/ml (~350 µM; FIG. 1)

ST104P Inhibited the Migration of Endothelial Cells

Figure 2:
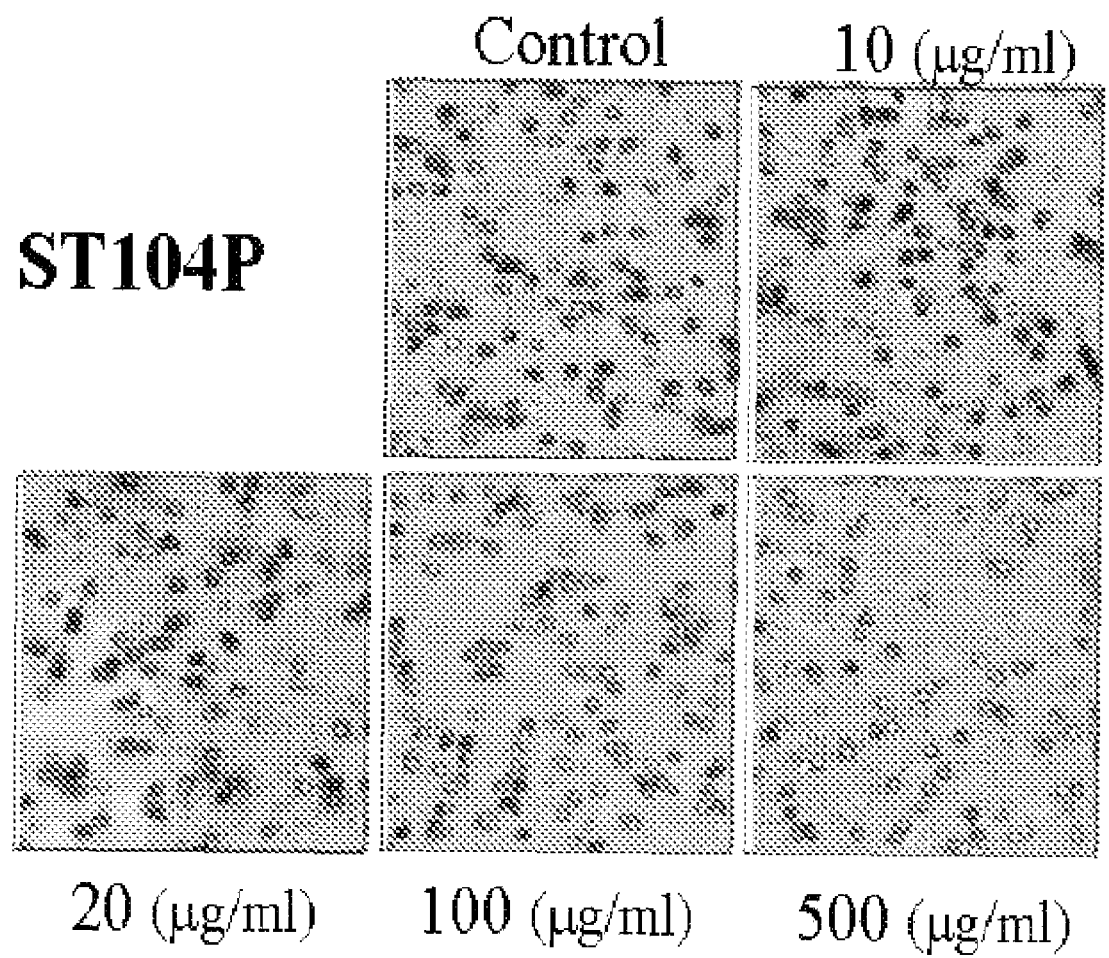
FIG. 2. ST104P inhibited the migration of endothelial cells. In order to evaluate the effect of ST104P on migration of endothelial cells, BAEC were plated in 6-well plate (1×10$^6$ cells per well) and treated with vasostatin of indicated dose for 12 h. After trypsinization, endothelial cells were applied to top wells in Boyden chamber to initiated migration toward chemoattractant bFGF (100 ng/ml) in the bottom wells. The migrated cells on filter were stained and counted. Each point represents mean±SEM of triplicate experiments.

To analyze the effect of ST104P on migration of endothelial cells, an in vitro migration system in Boyden chamber was exploited with bFGF as chemoattractant. After incubation with endothelial cells for 6 h, ST104P treatment prominently inhibited the migration of endothelial cell toward chemoattractant bFGF in a dose-dependent manner ($IC_{50}$ 100 µg/ml for BAEC and EA.hy926; FIG. 2)

ST104P Perturbed the Tube Formation of Endothelial Cells

The abilities of endothelial cells to form tube-like structure in the presence of ST104P were also investigated. Application of ST104P (20-100 µg/ml) effectively abolished the vessel-like structure of BAEC or EA.hy926 cells in Matrigel (FIGS. 3A and 3B)

Tube Formation MMP Secretion

Figure 4:
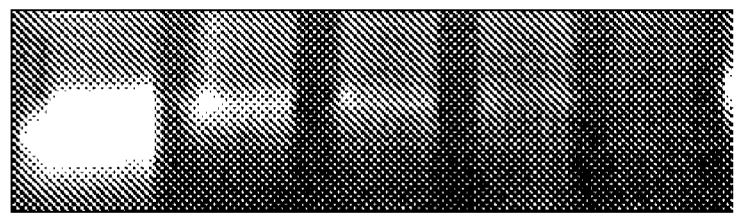
FIG. 4 shows the effect of ST104P on MMPs secretion by endothelial cells. ST104P decreases the MMPs secretion by endothelial cells. The conditioned media of BAECs or EA.hy926 cells (in 24-well plate at $1 \times 10^4$ cells/well) treated with PBS or ST104P (10-500 µg/ml) for 24 h were collected to analyze the expression of MMPs by gelatin-PAGE zymography.
Figure 4:
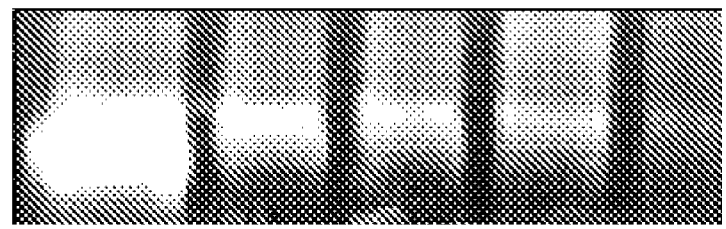

Angiogenesis can be divided into several distinct steps including matrix metalloproteinases (MMPs) secretion, proliferation and migration of endothelial cells. Thus, we examined the effects of ST104P on these angiogenic processes in BAEC and EA.hy926 cells. MMPs, a family of zinc-containing endopeptidase, mediate selective degradation of extracellular matrix that is required for migration and invasion of endothelial cells at the onset of angiogenesis. To determine the effect of ST104P on MMPs secretion, the conditioned media from ST104P-treated endothelial cells were subjected to gelatin-zymography analysis. ST104P potently inhibited the secretion of MMP-2 and MMP-9 by endothelial cells even at dose as low as 10 µg/ml (FIG. 4). These data suggested that ST104P may affect the de novo synthesis or release of MMPs in endothelial cells.

ST104P Inhibited Angiogenesis Chicken Choroiallantoic Membrane

Figure 5:
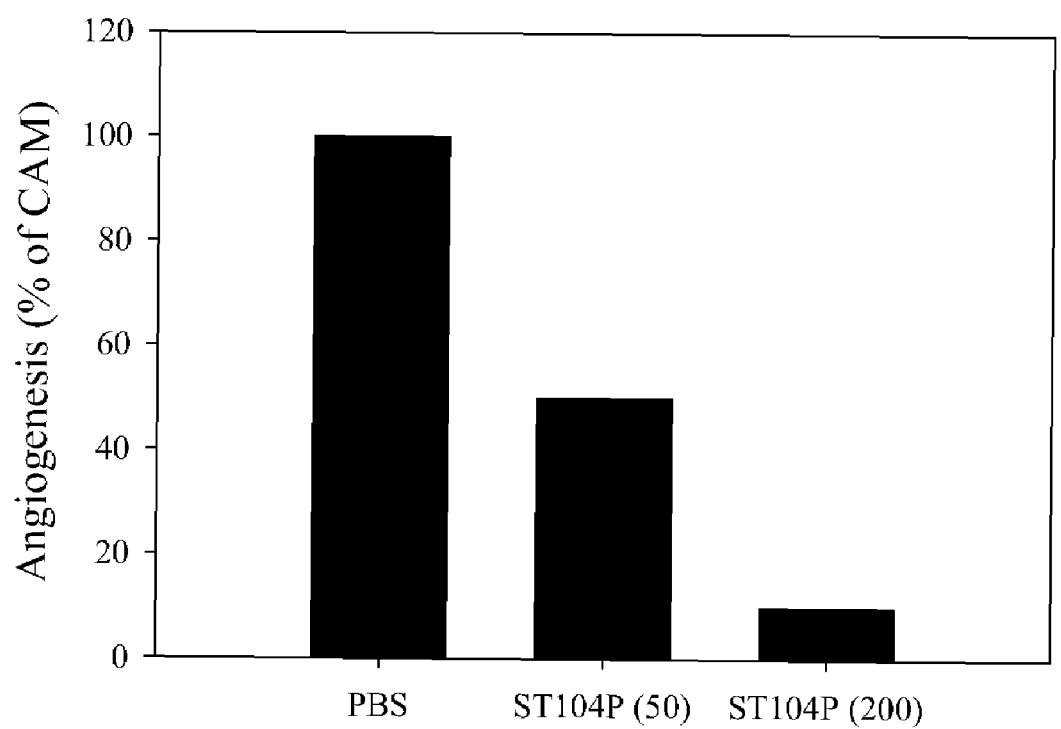
FIG. 5 shows the effect of ST104P on neovascularization in chicken embryos. The CAMs in 8-day old chicken embryos were incubated with saline or ST104P (50 or 200 µg in saline) for 48 h. The angiogenesis profiles on CAMs were recorded under dissection microscope. There was active and intact blood vessels formation in PBS-treated CAM. In contrast, the vascular network was severely destroyed in ST104P-treated CAMs.

To study the ability of ST104P in inhibiting angiogenesis in vivo, we used the CAM assay in 8-day old chick embryos because extensive neovascularization occurs during that period. At a dose of 50 µg per CAM, there was 50% inhibition of angiogenesis in ST104P-treated CAM, whereas, PBS had no obvious effects on neovascularization in CAMs nor on the mortality rate of chicken embryos (FIG. 5). At an escalated dose of 200 µg per CAM, the extensive inhibition of neovascularization by ST104P led to 90% mortality of chick embryos (9 out of 10 died in ST104P-treated groups versus 0 in PBS-treated group). These data indicated that ST104P abolished the neovascularization during chicken embryo development.

Repeated Injection of ST104P Suppressed the Tumor Growth in Mice

Figure 6:
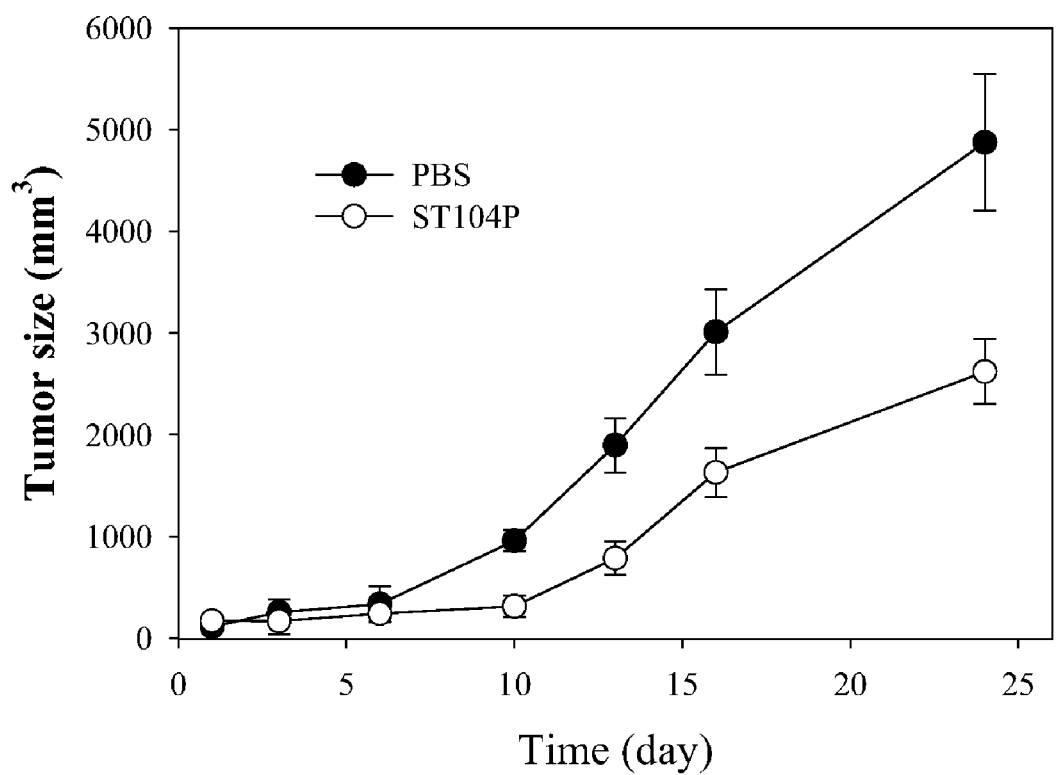
FIG. 6. Injection of ST104P suppressed tumor growth of Lewis lung carcinoma in mice. The subcutaneous dorsa of mice were implanted with Lewis lung carcinomas. The tumor sizes in mice during treatment with ST104P or control were recorded. Treatment was performed by intratumor injection of ST104P (100 µg in 0.1 ml PBS) daily from day 0 to day 10 as indicated by horizontal bar. Each point represents mean±SEM for ten mice. The experiment was repeated with comparable results.
Figure 7:
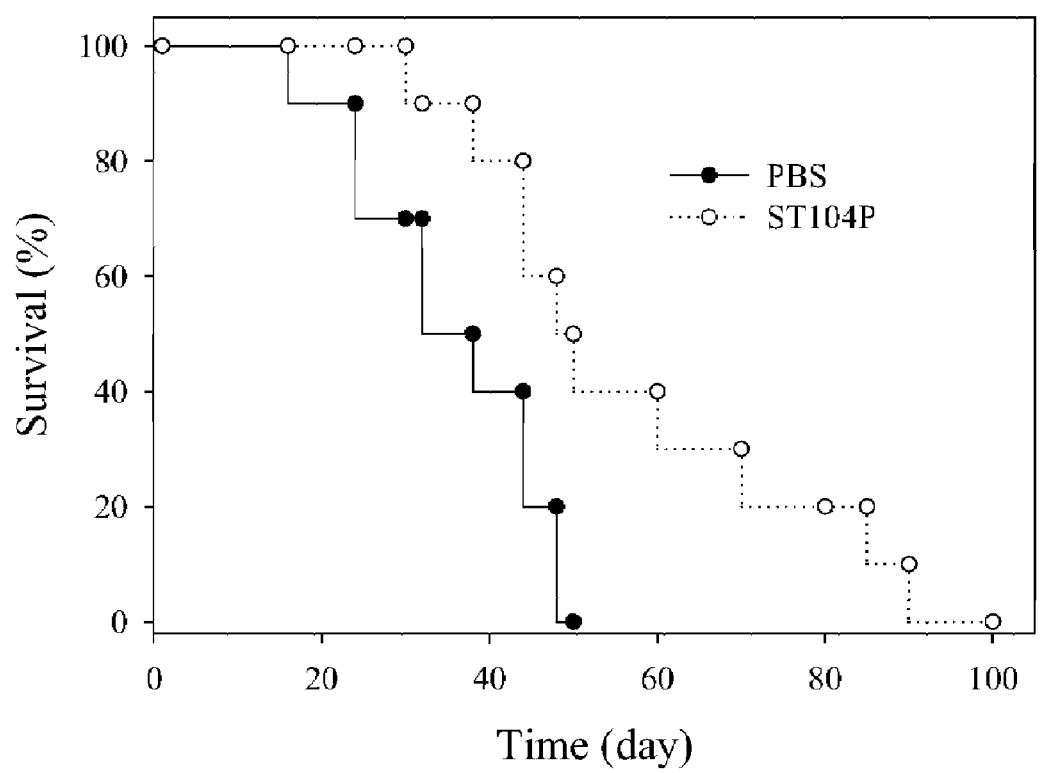
FIG. 7. Injection of ST104P prolonged the survival of tumor-bearing mice. The subcutaneous dorsa of mice were implanted with Lewis lung carcinomas. The tumor sizes in mice during treatment with ST104P or control were recorded. Treatment was performed by intratumor injection of ST104P (100 µg in 0.1 ml PBS) daily from day 0 to day 10 as indicated by horizontal bar. Each point represents mean±SEM for ten mice. The overall survival rates of ten mice in PBS- or ST104P-treated group were recorded. Kaplan-Meier survival analysis indicated the ST104P treatment significantly enhanced the survival rates of tumor-bearing mice ($P<0.001$). The experiment was repeated with comparable results.
Figure 8:
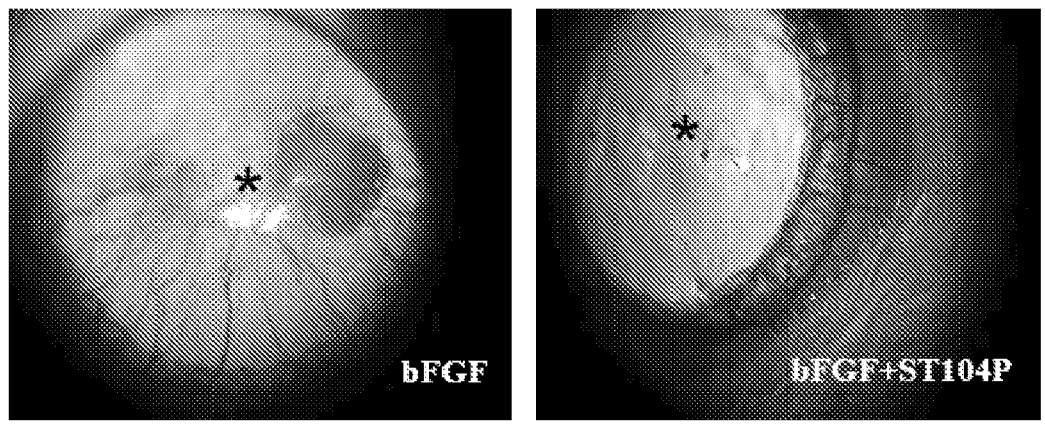
FIG. 8. Inhibition of basic fibroblast growth factor (bFGF)-induced corneal angiogenesis by incorporation of ST104P in a hydron polymer. (A) Representative corneas after implantation of bFGF pellet (100 ng per pellet; left panel) or pellet containing bFGF plus ST104P (100 ng for bFGF and 500 ng for ST104P per pellet; right b) for 7 days. The asterisk represents the place of hydron pellet implantation. (B) The neovascularization in rat corneas after implantation bFGF hydron pellets or pellets containing bFGF and ST104P. The length (panel a) and area (panel b) of neovascularized vessels in rat corneas were measured after implantation for 3-7 days. Data are means±SEM (n=8 per group). *$P<0.01$.
Figure 8:
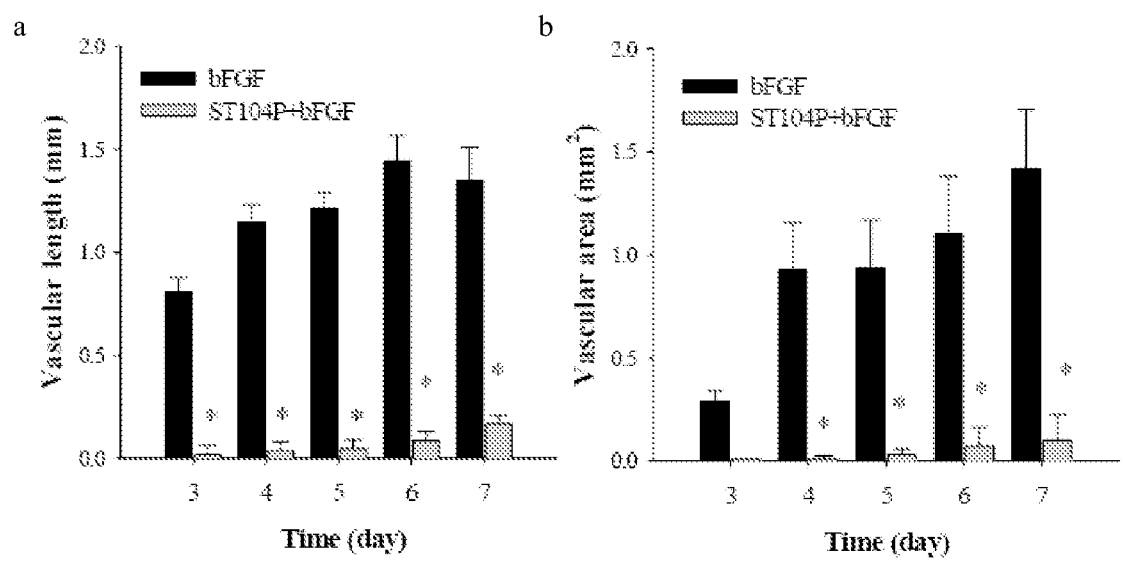
Figure 9:
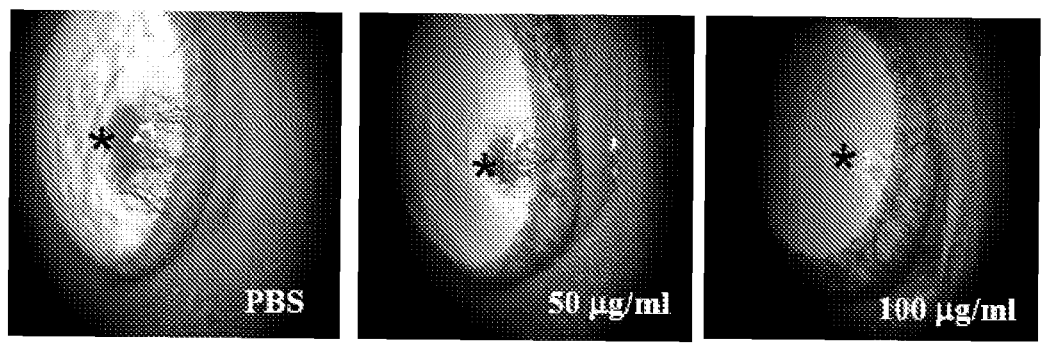
FIG. 9. Inhibition of corneal angiogenesis by topical application of ST104P. (A) Representative photographs of basic fibroblast growth factor (bFGF)-implanted corneas after topical application of control (phosphate buffered saline, PBS) eye drop (left panel) and ST104P-containing eye drop (50 µg/ml, middle panel; 100 µg/ml, right panel) for 7 days. The asterisk represents the place of hydron pellet implantation. (B) The dose-dependent effect of topical ST104P application on bFGF-induced corneal angiogenesis. After implantation of bFGF pellets, the mean vessel length and vascularized area in rat corneas treated with phosphate buffered saline eye drops or ST104P eye drops (10-100 µg/ml) were measured on day 7 (*$P<0.05$; **$P<0.01$). Data represent mean±SEM (n=8 per group).
Figure 9:
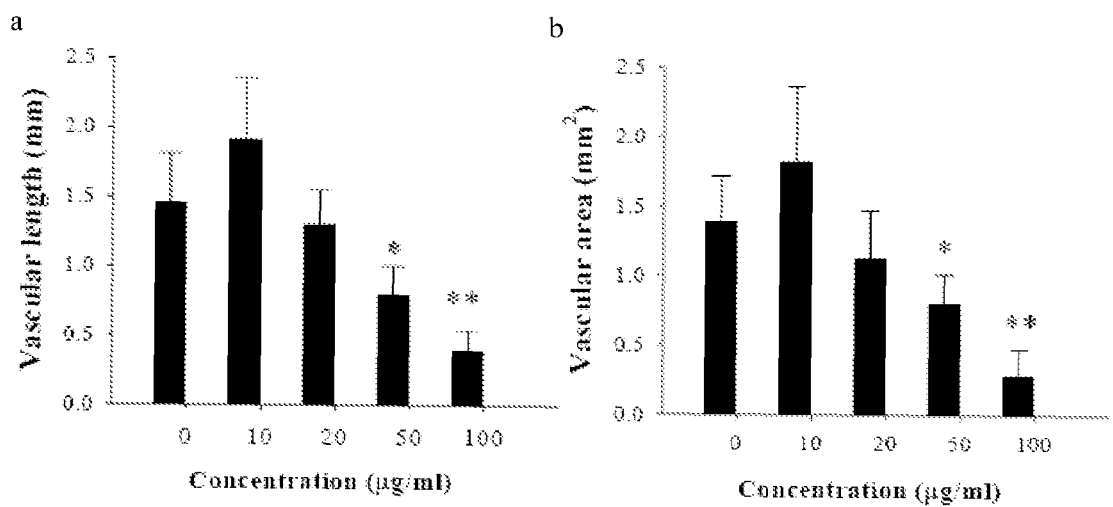
Figure 10:
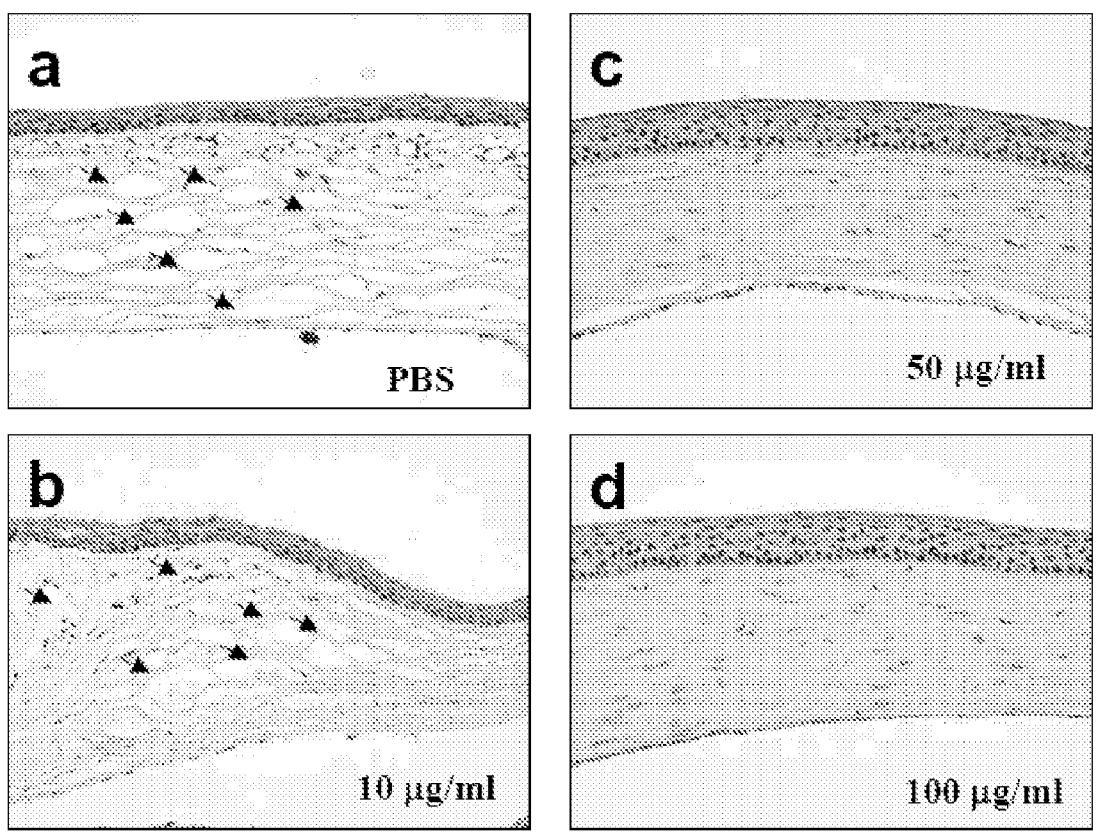
FIG. 10. Histological analysis of basic fibroblast growth factor (bFGF)-implanted rat cornea after ST104P eye drop treatment. After eye drop treatment for 7 days, the bFGF-implanted rat corneas were harvested and stained with hematoxylin and eosin (200×). In eyes that received the control PBS eye drop (a) or low dose ST104P eye drop (10 µg/ml, b), multiple lumen-like formations containing red blood cells presented in the corneal stroma (arrowhead) with the bFGF implant. Neocapillaries (arrowheads) are prominent in the corneal stroma. The intervening stroma exhibits edema and a mononuclear inflammatory response. There is no significant neovascularization shown in eyes receiving high dose ST104P eye drops (50 and 100 µg/ml respectively in c, d) and edema or inflammatory responses. The ST104P treated cornea appears normal histologically without apparent adverse effects.

We treated established Lewis lung carcinoma grown in syngeneic C57BL/6J mice by periodic intratumor injection of ST104P into tumors. The growth of Lewis lung primary tumors was suppressed by subcutaneous injection of ST104P (100 µg) for four times that the average tumor size of ST104P-treated mice (2620±320 mm$^3$) was significantly smaller (~40% decrease) than that of saline-treated groups (4876±670 mm$^3$; P<0.05; FIG. 6). In addition, mice treated with ST104P survived significantly longer than animals of vehicle-treated group (P<0.01; FIG. 7). There was no evident weight loss or adverse effects in mice treated with ST104P suggesting that ST104P injection was well tolerated by animals. Together, these results indicate that ST104P may be applicable to cancer therapy.

Discussion

In the present study, we demonstrate that ST104P is a potent inhibitor for MMP secretion and formation of tube-like structure in endothelial cells. The inhibitory mechanism of ST104P in CAM angiogenesis and tumor growth seems to be mediated via its anti-angiogenic effects. Unlike other angiogenesis inhibitor such as TNP-470 (Moulton et al., Circulation 99, 1726-1732, 1999), angiostatin (O'Reilly et al., Cell 79, 315-328, 1994), or endostatin (O'Reilly et al., Cell 88, 277-285, 1997), ST104P does not directly inhibit the proliferation of endothelial cells. Instead, ST104P indirectly suppressed angiogenesis via blockade of other angiogenesis steps such as migration, tube formation, and MMP secretion. In contrast to TNP-470 or endostatin, ST104P is soluble and could be administrated via saline or buffer systems. Recently, human clinical trials on MMP inhibitors have been completed and yielded differential outcomes. Because of the high potency in halting MMP secretion, ST104P may enter clinical trials as based on its indication as MMP inhibitor.

Because of its low cytotoxicity, ST104P treatment was well tolerated by animals via various routes including oral or intravenous, intraperitoneal, and intratumor injection without overt signs of adverse effects (data not shown). Future studies on the toxicology, pharmokinetics and biodistribution of ST104P are warranted to gain further insights in the safety and side effects of ST104P. Since ST104P is an aromatic compound, the carcinogenic potential should be extensively evaluated during pre-clinical trial. In summary, ST104P is a soluble angiogenesis inhibitor with low cytotoxicity that may hold potential for future clinical application.

Example 2

Materials and Methods

Corneal Angiogenesis

The sustained-release polymer pellets were made of the slow-release hydron polymer (polyhydroxyethylmethacrylate, polyHEMA; Sigma, St. Louis, Miss.) that contained sucralfate, bFGF (100 ng per pellet; R & D Systems, Minneapolis, Minn.), and/or ST104P (100-1000 ng per pellet). All rats were handled in accordance with the Association for Research in Vision and Ophthalmology Resolution on the Use of Animals in Research. Male Sprague-Dawley rats (300-350 g, Animal Center, National Science Counsel, Taipei, Taiwan) were used in this study. All surgical procedures were performed using sterile techniques. The rats were placed under anesthesia with 3% isoflurane in an O$_2$/room air mixture (1:1). Additional topical anesthesia (0.4% benoxinate hydrochloride, Ciba Vision Ltd., Hettlingen, Switzerland) was applied to the corneal surface. The eyes were exposed by grasping the temporal limboconjunctiva using a jeweler's forceps and the central-peripheral corneal intrastromal lamellar pocket (0.6×1.5×1 mm for depth×length×width) was dissected with a surgical blade (Paragon no. 11; Maersk Medical LTD, Sheffield, England). The pockets were extended 1.5 to 2 mm away from the limbus. The pellet was grasped by smooth forceps from the refrigerator (−20° C.) and immediately implanted into the corneal stromal pocket in each eye. Topical antibiotic ointment (0.3% gentamycin; Alcon Cusi, Spain) was applied to the corneal surface to reduce irritation and prevent infection.

Implanting Hydron Pellets

The corneal micropockets of rats were implanted with the following hydron pellets: bFGF pellets (100 ng per pellet), bFGF+ST104P pellets (100 ng bFGF and 500 ng ST104P per pellet), ST104P pellets (500 ng or 1000 ng per pellet), and phosphate buffered saline (PBS) pellets that were free of protein.

Topical Application of ST104P

Rat eyes were implanted with hydron pellets containing bFGF (100 ng per pellet) then treated with 50 µl of methylcellulose eye drops (2% Methocel, Novartis Ophthalmology AG, Hettlingen, Switzerland) containing PBS or ST104P (final concentration of 10-100 µg/ml) three times daily.

Biomicroscopic Examination

Examinations were made with a dissecting microscope and results were photographed on days 3, 5 and 7. Under anesthesia, the maximum vessel length and width of the neovascularization in rat eyes were measured and calibrated using a microscale (Nikon, Tokyo, Japan). The area of neovascularization of the cornea was determined from the dimensions of the triangular growth pattern of the vessels. Photographs of the corneal angiogenesis assay were obtained and digitized in a 640×480 pixel matrix, using a digital camera CoolPix 995 (Nikon, Tokyo, Japan). The operator was blinded to experimental design. Areas containing blood vessels were traced on the computer monitor and calculated with image analysis software (Scion Image 4.02; Scion, Maryland, USA) and reported in square millimeters with determinations. The biomicroscopic assessment was conducted by two independent observers.

Histological Analysis

After treatment, the rat corneas were dissected and fixed in paraffin. The paraffin-embedded tissues were sectioned in 5-μm slices, mounted on poly-L-lysine-coated slides and subjected to hematoxylin and eosin staining.

Statistical Analysis

To analyze the differences between groups, Mann-Whitney U test analysis with two-tailed probability was used and a P value of less than 0.05 was considered significant. Results are presented as means±SEM (standard error of the mean). For each experiment, surgery was performed on all animals in a standardized fashion, and animals were randomized to the different treatment and control groups.

Results

Incorporation of ST104P Attenuated bFGF-Induced Corneal Angiogenesis

To evaluate the efficacy of ST104P in vivo, hydron pellets containing bFGF, ST104P, or bFGF plus ST104P were implanted into rat corneas to monitor the development of neovascularization. PBS pellets with no protein represented blank controls. Implantation of bFGF-containing pellets induced corneal angiogenesis within 3-7 days (Table 1). In contrast, implantation of ST104P or PBS pellets did not induce neovascularization in rat corneas. However, implantation of pellets containing bFGF plus ST104P resulted in significantly reduced corneal neovascularization comparing with that in eyes implanted with bFGF pellets (FIG. 1). At day 7, ST104P incorporation significantly decreased the length (1.36±0.4 mm for bFGF pellets versus 0.17±0.06 mm for pellets containing bFGF plus ST104P; P<0.01) and area (1.42±0.28 mm$^2$ for bFGF pellets versus 0.12±0.11 mm$^2$ for pellets containing bFGF plus ST104P; P<0.01) of bFGF-induced blood vessels. These results indicated that concomitant addition of ST104P potently perturb bFGF-mediated corneal angiogenesis.

TABLE 1

Mean length of new vessels and area of neovascularization upon administration of ST104P and phosphate buffered saline (PBS) on basic fibroblast growth factor (bFGF)-induced angiogenesis in rat corneas on day 7.

| Pellets | No. of eyes | Length (mm) | Area (mm$^2$) |
| --- | --- | --- | --- |
| PBS | n = 8 | 0 | 0 |
| ST104P (500 ng) | n = 8 | 0 | 0 |
| ST104P (1000 ng) | n = 8 | 0 | 0 |
| bFGF | n = 16 | 1.36 ± 0.40 | 1.42 ± 0.28 |
| bFGF + ST104P | n = 8 | 0.17 ± 0.06* | 0.12 ± 0.11* |

After implantation of various hydron pellets for 7 days, neovascularization of rat corneas was measured using image analysis. The dose of bFGF and ST104P in each pellet was 100 ng and 500 ng, respectively.
*P < 0.01 versus bFGF group.
PBS represents blank control pellet containing no investigative protein.
bFGF + ST104P means concomitant addition of bFGF with ST104P in the hydron pellet.

Topical ST104P Application Inhibited bFGF-Induced Corneal Angiogenesis

Figure 3:
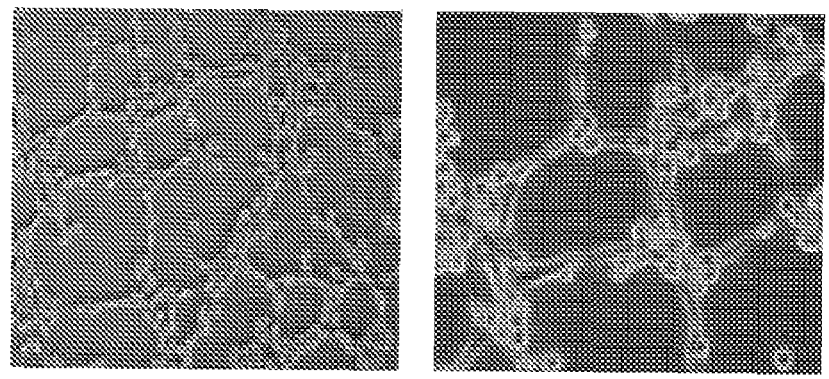
FIG. 3. ST104P abolished the tube formation of endothelial cells. Application of ST104P perturbed tubular network of BAEC or EA.hy9236 cells in Matrigel. Endothelial cells were applied to Matrigel-coated plate in the absence or presence of ST104P. After 8 h, the tubular structures of BAEC cells were monitored and recorded under light microscopy. The pictures were taken at 400× magnification.
Figure 3:
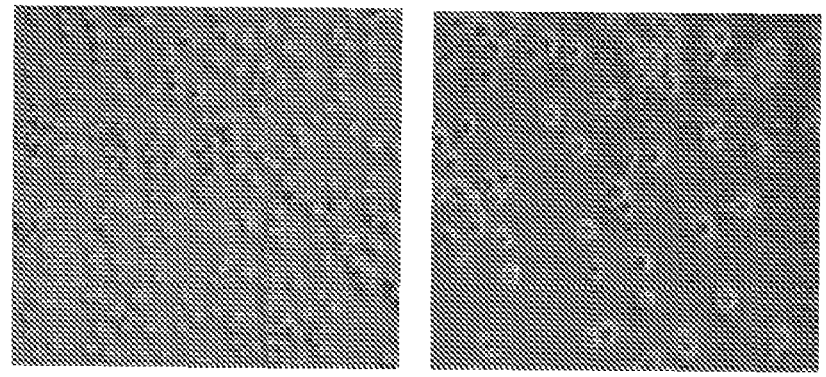
Figure 3:
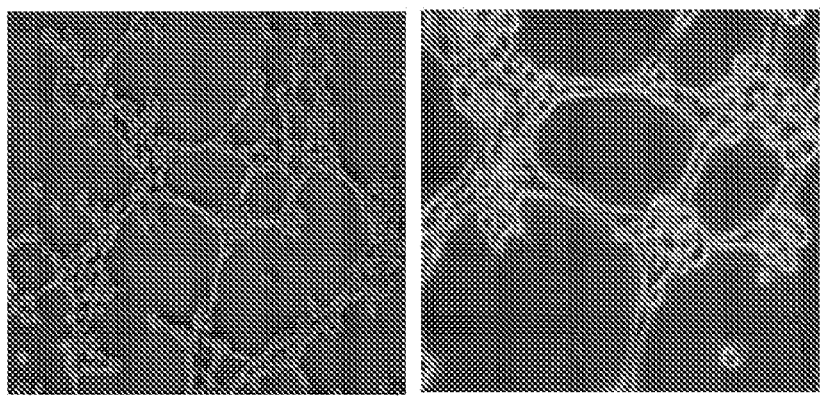
Figure 3:
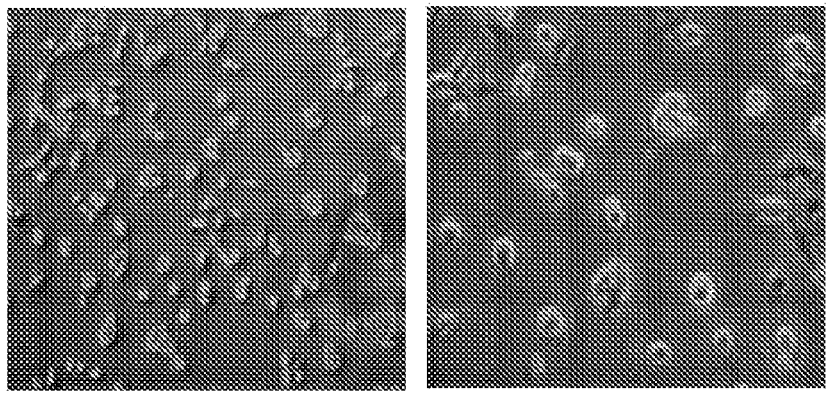

To evaluate the efficacy of ST104P on corneal angiogenesis, bFGF pellets were implanted into both eyes of rats. Subsequently, one eye was treated with PBS-based eye drop and the other was treated with ST104P-containing eye drop (10-100 μg/ml) three times daily. Topical application of ST104P significantly reduced the vessel length and vascularized area of the bFGF-implanted corneas in a dose-dependent manner (FIG. 2). The ST104P eye drop at the concentration of 10-20 μg/ml did not elicit inhibitory effect on bFGF-induced cornea angiogenesis. However, ST104P eye drop at the concentration of 100 μg/ml significantly suppressed cornea angiogenesis that the average vessel length in corneas treated with ST104P eye drops was prominently decreased compared with that of corneas treated with the PBS eye drop (0.39±0.15 mm versus 1.36±0.4 mm; P<0.01). Furthermore, the neovascularized area in ST104P-treated corneas was also significantly attenuated (0.28±0.19 mm$^2$) compared to that of PBS-treated corneas (1.42±0.28 mm$^2$; P<0.01). Histological analysis revealed that application of ST104P eye drops prominently inhibited corneal angiogenesis without overt cytotoxicity to the other eye cells (FIG. 3). Together, these results strongly support that implant application or topical eye drop application of ST104P for effective suppression of corneal angiogenesis without apparent toxicity.

Other diseases or conditions that are commonly known in the art to be mediated by angiogenesis and which can be treated by an angiogenesis inhibitor such as ST104P according to the invention are as follows:

Atherosclerosis

Neovascularization within the intima of human atherosclerotic lesions is well described. In normal vessels, the microvascular network of vasa vasorum is confined to the adventitia and other media. However, in vessels with atherosclerotic involvement, these networks become more abundant and extended to the intima of atherosclerotic lesions. Plaque vessels are often found in areas rich in macrophages T cells and mast cells, which cell types are known to activate angiogenesis. On of the main factors associated with atherosclerosis is oxidized low-density lipoprotein (LDL), which also causes apoptosis of endothelial cells. It has been demonstrated that endostatin is beneficial to endothelial cell growth exposed to mildly oxidized LDL and significantly reduce atherosclerosis in genetically susceptible mice (Ren et al, Methods Find Exp Clin Pharmacol, 24(4):159-199; 2002). In addition, prolonged treatment with angiogenesis inhibitors such as endostatin or TNP-470 reduced plague growth and intimal neovascularization in apolipoprotein E-deficient mice (Moulton et al., Circulation 1999; 99: 1726-1732)

Rheumatoid Arthritis

Inflammatory joint diseases such as rheumatoid arthritis (RA) are a major cause of disability and are frequently associated with increased morbidity and mortality. During the rheumatoid arthritis there is enlargement and increased cellularity of the synovial lining of joints, before invasion by the synovium of the underlying cartilage and bone. The increased tissue mass requires a network of blood vessels to supply nutrients and oxygen. Disruption of synovial angiogenesis is thus a desirable aim of antiarthritic therapies. It has been shown that the angiogenesis inhibitor, protease-activated kringles 1-5, reduces the severity of murine collagen-induced arthritis. The clinical efficacy of this treatment was reflected by a reduction in joint inflammation and destruction, which further suggests that antiangiogenic therapies that block formation of new blood vessels and reduce synovial expansion can be effective in treating rheumatoid arthritis (Sumariwalla et al, Arthritis Research and Therapy; 15(1)32-39, 2002). In addition, systemic administration of endostatin in passive murine collagen induced arthritis exhibits inhibition of arthritis by inhibiting pannus formation and bone destruction (Kurosaka et al, Ann Rheum Dis, 62; 677-697, 2003).

Systemic Lupus

Agent exhibiting anti-inflammatory and immunomodulatory activity also shows activity in treatment of systemic lupus (Alfadley et al., J Am Acad Dermatol, 48(5) S89-S91, 2003; Housman et al, Arch Dermatol, 139:50-54, 2003; Ossandon et al, Clinical and Experimental Rheumatology 2002, 20:709-718, U.S. Pat. No. 6,518,298) Cutaneous manifestations of lupus erythematosus are chronic, disfiguring lesions that may be associated with systemic diseases. These cutaneous lesions can be simply classified into 3 categories: (1) vascular lesions seen in systemic lupus erythematosus; (2) interface lesions seen in chronic cutaneous lupus erythematosus; or (3) special lesions as seen in lupus erythematosus profundus or in vesiculobullous lesions. It has been reported that thalidomide, an anti-inflammatory agent and an immunomodulator exhibiting anti-angiogenic activity, provides dramatic improvement to patients with systemic as well as cutaneous lupus erythematosus. (Alfadley et al., J Am Acad Dermatol, 48(5) S89-S91, 2003; Housman et al, Arch Dermatol, 139:50-54, 2003; Ossandon et al, Clinical and Experimental Rheumatology 2002, 20:709-718, U.S. Pat. No. 6,518,298).

Osteoarthritis

Angiogenesis may also have a role in osteoarthritis. Destruction of the joint is shown to be caused by the activation of the chondrocytes by angiogenic-related factors, which would subsequently promote new bone formation. Accordingly, therapeutic intervention that prevents the bone destruction could stop the progress of the disease and provide relief for persons suffering with arthritis (Smith J O, et al., J. Orthop Sci., 8; 849-857, 2003)

Age-Related Macular Degeneration

Age-related macular degeneration (ARMD) is a major cause of acquired blindness, which results from development of choroidal neovascularization associated with overlying retinal damages. Choroidal neovascularization is also generated in high myopia, angioid streaks, and some inflammatory diseases. Angiostatin, a known inhibitor of vessel endothelial proliferation in vitro and vessel growth inside tumors, is also shown to significantly reduce the sizes of choroidal neovascularization lesion (Lai et al, Investigative Ophthalmology and vessel Science, vol. 42 (10):2401-2407, 2001)

Diabetic Retinopathy

Antiangiogenic agents have been clinically studied in the treatment of retinal disease for patient with central retinal vein occlusion, branch retinal vein occlusion and diabetic retinopathy. For instances, vascular endothelial growth factor (VEGF), a mediator for angiogenesis in many experimental and clinical situation, is also a potent "vascular permeability factor" in inducing leakage of blood vessels. Evidence has accumulated linking upregulation of VEGF with both increased permeability of ocular blood vessels and the development of neovascularization in the eye. In monkey eyes, vascular leakage, like diabetic retinopathy, can be induced by injection of VEGF. And in diabetic animals and diabetic patients, there appears to be an early upregulation of VEGF, which can be responsible for the development of the retinopathy including neovascularization. Thus, agents that inhibit VEGF are potential therapeutic agents for both diabetic retinopathy and age-related macular degeneration. (Jampol, L. M.; Disclosure of American Academy of Ophthalmology 2002 Annual Meeting; October 18-9, Orlando, Fla.; Hans-Peter Hammes; Ocular Complications in Diabetes, 59th Annual Scientific Sessions of ADA, San Diego, Calif. 1999)

Retinal/Choroidal Neovascularization

Diseases associated with retinal/choroidal neovascularization include, but are not limited to, diabetic retinopathy, macular degeneration, sickle cell anemia, sarcoid, syphilis, pseudoxanthoma elasticum, systemic lupus erythematosis, vein occlusion, artery occlusion, carotid obstructive disease, chronic uveitis/vitritis, mycobacterial infections etc. Other diseases include, but are not limited to, diseases associated with rubeosis (neovascularization of the angle) and diseases caused by the abnormal proliferation of fibrovascular or fibrous tissue including all forms of proliferative vitreoretinopathy (U.S. Pat. No. 6,518,298.)

All referenced patents, applications and literatures are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A method of inhibiting undesirable angiogenesis of a non-tumor condition or disease in a human or animal comprises administering thereto an effective angiogenesis inhibiting dose of a tetrameric cyclic compound of 4,5-dihydroxynaphthalene-2,7, disulfonic acid linked by methylene bridges having the formula,

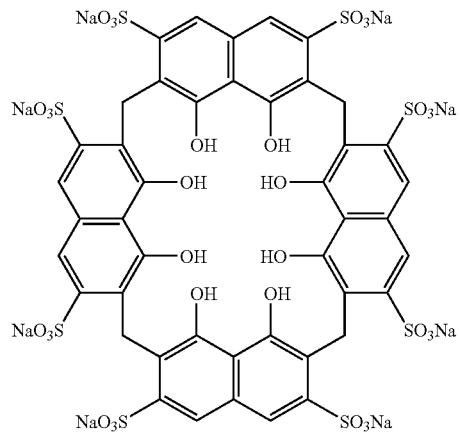

in a pharmaceutically acceptable carrier.

2. The method of claim 1, wherein the undesirable angiogenesis occurs in diabetic retinopathy.

3. The method of claim 1, wherein the undesirable angiogenesis occurs in sickle cell anemia.

4. The method of claim 1, wherein the undesirable angiogenesis occurs in vein occlusion.

5. The method of claim 1, wherein the undesirable angiogenesis occurs in artery occlusion.

6. The method of claim 1, wherein the undesirable angiogenesis occurs in age-related macular degeneration.

7. The method of claim 1, wherein the undesirable angiogenesis occurs in atherosclerosis.

8. The method of claim 1, wherein said condition or disease is rheumatoid arthritis.

9. The method of claim 1, wherein said condition or disease is systemic lupus.

10. The method of claim 1, wherein said condition or disease is osteoarthritis.

11. The method of claim 1, wherein said undesirable angiogenesis is corneal neovascularization.

12. The method of claim 1, wherein the pharmaceutically acceptable carrier is adapted for oral, sublingual, rectal, vaginal, nasal, transdermal, ophthalmic, topical, implant or parenteral administration.

13. The method of claim 12, wherein the ophthalmic administration is implant, topical, intravitreal or intracameral.

14. The method of claim 1, wherein the pharmaceutically acceptable cater is adapted in the form of a tablet, a capsule, a cachet, a solution, an emulsion, a depository, an implant, eye drop or a powder.

* * * * *